United States Patent [19]
Allard et al.

[11] Patent Number: 5,676,664
[45] Date of Patent: Oct. 14, 1997

[54] ORTHOPAEDIC DISTRACTOR AND/OR FIXATOR

[75] Inventors: Randall N. Allard, Plymouth; Charles D. Persons, Columbia City; Gregory G. Price; Joel Bales, both of Warsaw, all of Ind.

[73] Assignee: Zimmer, Inc., Warsaw, Ind.

[21] Appl. No.: 562,724

[22] Filed: Nov. 27, 1995

[51] Int. Cl.$^6$ ................................. A61B 17/60
[52] U.S. Cl. ................ 606/57; 606/54; 606/59
[58] Field of Search ................ 606/57, 58, 59, 606/61, 97, 53, 54, 56

[56] References Cited

U.S. PATENT DOCUMENTS

| | | | |
|---|---|---|---|
| 1,869,726 | 8/1932 | Youngren | 606/57 |
| 1,997,466 | 4/1935 | Longfellow | 606/57 |
| 2,391,693 | 12/1945 | Ettinger | 606/57 |
| 4,356,571 | 11/1982 | Esper et al. | 3/1 |
| 4,502,473 | 3/1985 | Harris et al. | 128/92 A |
| 4,893,618 | 1/1990 | Herzberg | 606/54 |
| 4,902,297 | 2/1990 | Devanathan | 623/16 |
| 4,978,348 | 12/1990 | Ilizarov | 606/57 |
| 4,978,350 | 12/1990 | Wagenknecht | 606/72 |
| 5,064,439 | 11/1991 | Chang et al. | 623/66 |
| 5,074,866 | 12/1991 | Sherman et al. | 606/54 |
| 5,152,687 | 10/1992 | Amino | 433/173 |
| 5,160,335 | 11/1992 | Wagenknecht | 606/59 |
| 5,163,962 | 11/1992 | Salzstein et al. | 623/23 |
| 5,181,930 | 1/1993 | Dumbleton et al. | 623/23 |
| 5,192,330 | 3/1993 | Chang et al. | 623/22 |
| 5,275,599 | 1/1994 | Zbikowski et al. | 606/54 |
| 5,397,358 | 3/1995 | Wenner et al. | 623/16 |
| 5,397,365 | 3/1995 | Trentacosta | 623/18 |
| 5,403,321 | 4/1995 | Di Marco | 606/97 |
| 5,405,347 | 4/1995 | Lee et al. | 606/54 |
| 5,443,464 | 8/1995 | Russell et al. | 606/54 |
| 5,443,513 | 8/1995 | Moumene et al. | 623/16 |
| 5,458,599 | 10/1995 | Adobbati | 606/56 |

FOREIGN PATENT DOCUMENTS

| | | | |
|---|---|---|---|
| 123279 | 1/1947 | Australia | 606/57 |

*Primary Examiner*—Michael Buiz
*Assistant Examiner*—Julian W. Woo
*Attorney, Agent, or Firm*—Todd A. Dawson

[57] ABSTRACT

The invention is directed to an apparatus for externally reducing and/or fixating a fracture in a bone. The apparatus includes a radiolucent rod, and a carriage assembly with a clamp assembly for connection to a fixation pin. A sleeve is threadingly connected with the carriage assembly and is disposed about the rod. A clamping device interconnects the sleeve with the rod at a selective one of a plurality of locations along a length of the rod. Rotation of the sleeve relative to the carriage assembly moves the rod in an axial direction relative to the carriage assembly.

7 Claims, 2 Drawing Sheets

ORTHOPAEDIC DISTRACTOR AND/OR FIXATOR

BACKGROUND OF THE INVENTION

1. Field of the invention

The present invention relates to external distractors and fixators for stabilizing a fractured bone, and, more particularly, to such distractors and fixators having a fixation rod interconnected to the fractured bone at a plurality of locations via a plurality of respective fixation pins.

2. Description of the related art

Orthopaedic apparatus for stabilizing a fracture in a bone may include structure for reducing and/or fixating the fracture in the bone. Distractors are used for reducing the fracture and fixators are used for fixating the fracture.

Distractors used for such reduction may include surgical fixation pins which are attached to the bone on each side of the fracture and secured to an external fixation rod. Distractors are used to move the portion of the bone on one side of the fracture relative to the portion of the bone on the other side of the fracture, whereby the bone portions may be properly aligned. A clamp assembly is used to interconnect the fixation pins to the fixation rod. The fixation rod is formed from a metal material and threadably engages one of the clamp assemblies so that the clamp assemblies can be moved toward or away from each other along the axial length of the rod.

Conventional fixation systems are used to hold a fractured bone in alignment during the healing process. Such fixators may include a fixation rod which is used to interconnect and rigidly secure a plurality of fixation pins inserted into the fractured bone at various points, with each fixation pin being retained within a clamp secured to the fixation rod. Each clamp is installed onto the fixation rod by sliding the clamp over one end or the other and tightening one or more nuts when the clamp is in its desired longitudinal position on the rod.

It is known to use a rod in a distractor or fixator which is constructed of a radiolucent material which does not interfere with X-rays. Such a fixation rod may be constructed, e.g., of a composite material in the form of fiberglass or graphite. Such materials are suitable for use in a fixation system where the rod is merely clamped in a radial direction by the clamp, but are not suitable for use in a distractor system where the rod is threaded and moved in an axial direction by rotation thereof. More particularly, such materials have a shear strength which is less than metal, thereby resulting in an increased probability of stripping the threads on the rod when the rod is rotated.

What is needed in the art is a radiolucent rod which can be used with a distractor system.

SUMMARY OF THE INVENTION

The present invention provides an orthopaedic distractor and/or fixator with a threaded metal sleeve interposed between and interconnecting a carriage assembly to a radiolucent rod.

The invention comprises, in one form thereof, an apparatus for externally reducing and/or fixating a fracture in a bone. The apparatus includes a radiolucent rod and a carriage assembly with a clamp assembly for connection to a fixation pin. A sleeve is threadingly connected with the carriage assembly and is disposed about the rod. A clamping device interconnects the sleeve with the rod at a selective one of a plurality of locations along a length of the rod. Rotation of the sleeve relative to the carriage assembly moves the rod in an axial direction relative to the carriage assembly.

An advantage of the present invention is that a radiolucent rod may be used in conjunction with a distractor.

Another advantage is that the distractor is operable upon rotation of the handle and attached rod, without stripping threads at the interconnection with the carriage assembly.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
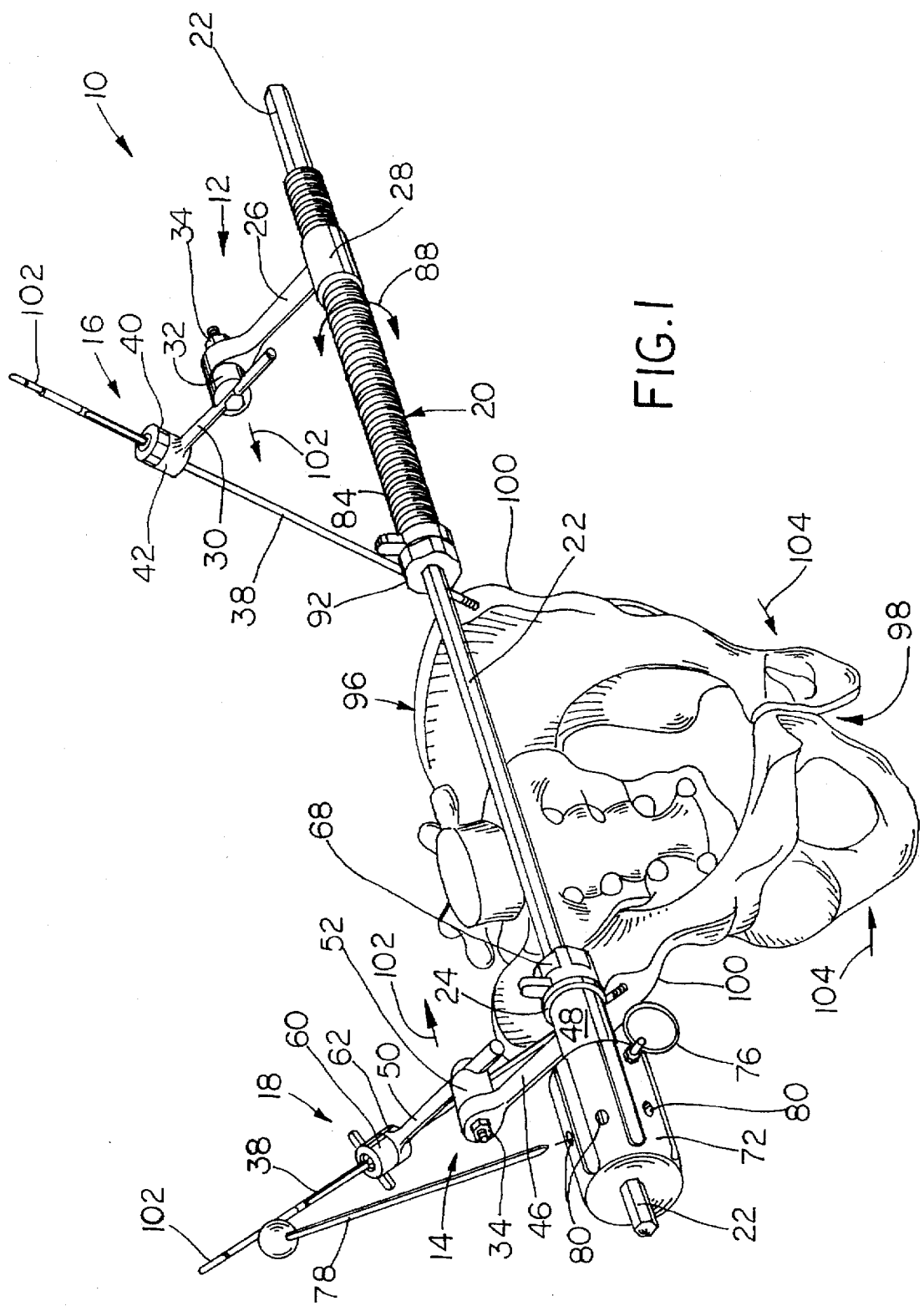
FIG. 1 is a perspective view of an embodiment of a pelvic distractor of the present invention.
Figure 2:
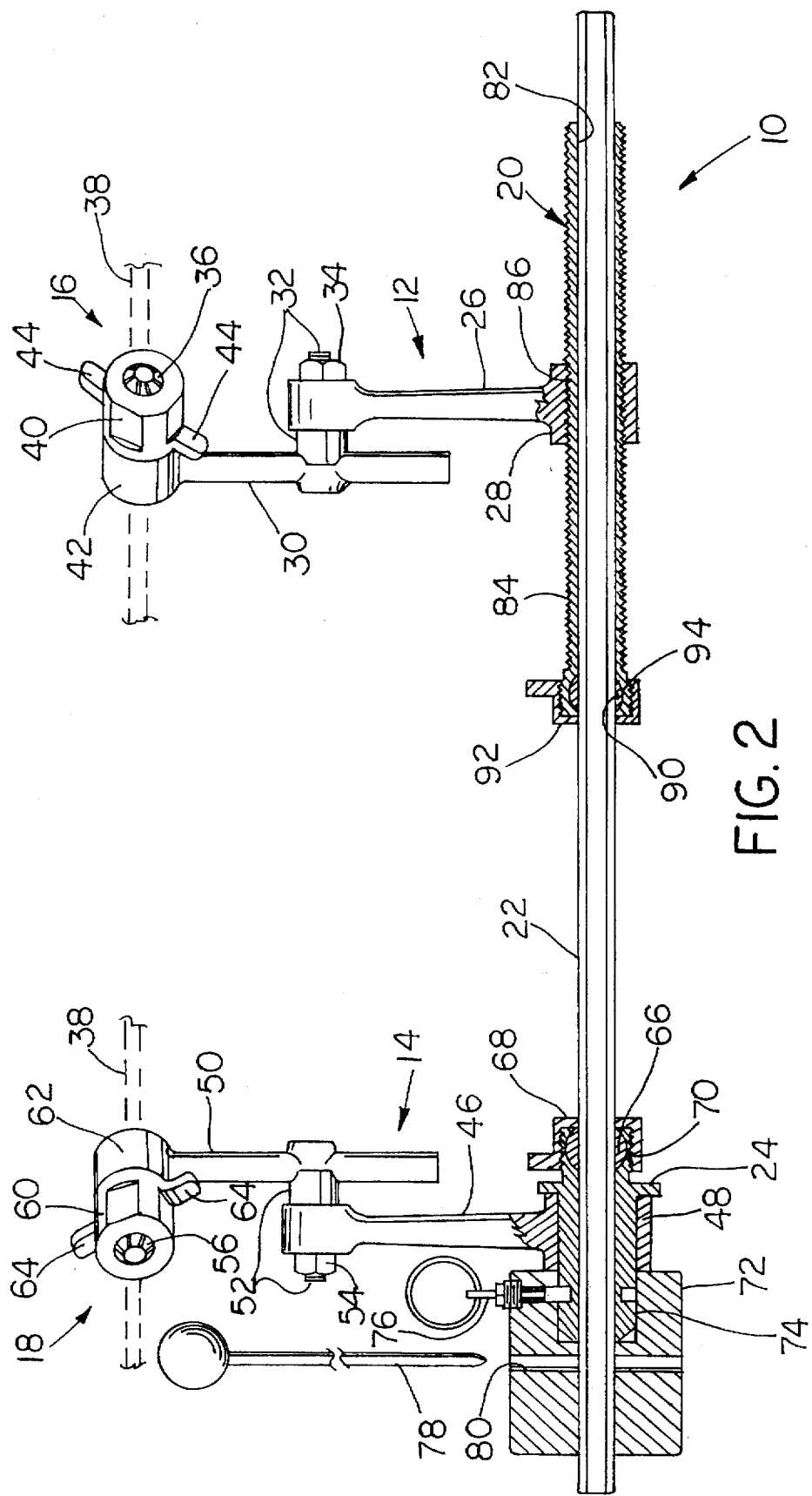
FIG. 2 is a side, sectional view of the pelvic distractor shown in FIG. 1.

Referring now to the drawings and particularly to FIGS. 1 and 2, there is shown an embodiment of an orthopaedic distractor 10 of the present invention. Of course, it will be appreciated to those skilled in the art that external distractor 10 can also be used as an external fixator. Distractor 10 generally includes carriage assemblies 12, 14 including respective clamp assemblies 16, 18, threaded sleeve 20, rod 22 and body 24.

Carriage assembly 12 includes an arm 26 with an internally threaded end 28 which threadably engages sleeve 20. Clamp assembly 16 includes an arm 30 which is adjustably connected to arm 26 via a threaded connector 32. A nut 34 is used to lock the relative position between arm 30 and arm 26. Clamp assembly 16 also includes a collet 36 which frictionally engages a fixation pin 38. A nut 40 is threadably engaged with a distal end 42 and biases collet 36 in a radially inward direction upon rotation thereof to frictionally engage fixation pin 38. Ears 44 of nut 40 provide increased leverage to a user for rotation of nut 40.

Carriage assembly 14 includes an arm 46 with an end 48 which pivotally engages body 24. Clamp assembly 18 includes an arm 50 which is adjustably connected to arm 46 via a threaded connector 52. A nut 54 is used to lock the relative position between arm 50 and arm 46. Clamp assembly 18 also includes a collet 56 which frictionally engages a fixation pin 38. A nut 60 is threadingly engaged with a distal end 62 and biases collet 56 in a radially inward direction upon rotation thereof to frictionally engage fixation pin 38. Ears 64 of nut 60 provide increased leverage to a user for rotation of nut 60.

Rod 22 is a radiolucent rod which interconnects carriage assemblies 12, 14. Rod 22 is constructed from a material, e.g., such as fiberglass, carbon, polyester or the like which does not interfere with X-rays. In the embodiment shown in the drawings, rod 22 has a hexagonal cross-section; however, rods with other cross-sections are also possible.

Body 24 is rigidly affixed to rod 22 using a collar 66 and nut 68. More particularly, nut 68 is threadingly engaged with body 24, as shown in FIG. 2. Tightening of nut 68 on body 24 results in an axial compression of collar 66 against body 24. Body 24 includes a concave surface 70 at the axial end thereof which biases collar 66 in a radially inward direction upon axial compression of collar 66 by nut 68.

A knob 72 includes an interior recess 74 which engages body 24. A release pin 76 passes through knob 72 and into body 24 to prevent relative rotational movement therebetween. A handle 78 may be inserted into one of a plurality of openings 80 in knob 72 to provide increased leverage to a user, and thereby allow easier rotation of rod 22 relative to carriage assemblies 12, 14.

Sleeve 20 interconnects rod 22 with carriage assembly 12. In the embodiment shown, sleeve 20 is a metal sleeve having an opening 82 extending through the length thereof in which rod 22 is disposed. Sleeve 20 includes exterior threads 84 which are threadingly connected with interior threads 86 of arm 26. Sleeve 20 is therefore rotatable relative to arm 26, as indicted by directional arrow 88 (FIG. 1).

In use, distractor 10 is affixed, e.g., to pelvis 96 and used to reduce a fracture, such as may occur at 98. More particularly, fixation pins 38 are each screwed into a respective ilium 100 of pelvis 96. A suitable tool is attached to distal end 102 of fixation pins 38 for turning fixation pins 38 into ilium 100. Nuts 40, 60, 68 and 92 are all loosened so that clamp assemblies 16, 18 may slide over fixation pins 38, and sleeve 20 and body 24 may slide over rod 22. Carriage assemblies 12, 14 are placed in a preferred position and nuts 34, 40, 60, 68 and 92 are all tightened. Knob 72 is affixed to body 24 using release pin 76, and knob 72 is rotated to rotate sleeve 20, which in turn moves carriage assembly 12 in an axial direction relative to rod 22. This in turn applies a force to fixation pins 38 in a direction parallel to rod 22, as indicated by arrows 102, which in turn reduces fracture 98, as indicated by arrows 104.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An apparatus for at least one of externally reducing and fixating a fracture in bone, comprising:
   a carriage assembly including a clamp assembly for connection to a fixation pin;
   a rod having a substantially smooth exterior surface;
   an externally threaded sleeve interconnecting said rod with said carriage assembly, said externally threaded sleeve being threadingly connected with said carriage assembly and disposed about said rod;
   said externally threaded sleeve defining an interior surface, said interior surface of the externally threaded sleeve being substantially smooth; and
   means engaging said smooth exterior surface of said rod for attaching said sleeve to said rod at a selective one of a plurality of locations along a length of said rod, wherein said sleeve is shiftable relative to said rod and is securable relative to the rod by said attaching means, wherein as said sleeve and rod are rotated relative to said carriage assembly the carriage assembly moves longitudinally along said sleeve.

2. The apparatus of claim 1, wherein said attaching means applies a radially inward force to said rod to hold said sleeve at said selected location.

3. The apparatus of claim 1, wherein said attaching means comprises a collar and a nut, said nut being threadingly engaged with said sleeve.

4. The apparatus of claim 3, wherein said nut is configured to deflect said collar in a radially inward direction and thereby apply a radially inward force to said rod.

5. The apparatus of claim 1, wherein said rod has a hexagonal cross-section.

6. The apparatus of claim 1, wherein said sleeve comprises a metal sleeve.

7. The apparatus of claim 1, wherein said sleeve has an opening extending through the length thereof, said rod disposed within said opening.

* * * * *